US010299512B2

(12) United States Patent
Spirito et al.

(10) Patent No.: US 10,299,512 B2
(45) Date of Patent: May 28, 2019

(54) DISPOSABLE ELECTRONIC-CIGARETTE CARTRIDGE AND RESPECTIVE PRODUCTION METHOD

(71) Applicant: G.D SOCIETA' PER AZIONI, Bologna (IT)

(72) Inventors: Gilberto Spirito, Bologna (IT); Stefano Negrini, Calderara Di Reno (IT)

(73) Assignee: G.D. SOCIETA'PER AZIONI, Bologna (IT)

( * ) Notice: Subject to any disclaimer, the term of this patent is extended or adjusted under 35 U.S.C. 154(b) by 292 days.

(21) Appl. No.: 15/127,830

(22) PCT Filed: Apr. 1, 2015

(86) PCT No.: PCT/IB2015/052411
§ 371 (c)(1),
(2) Date: Sep. 21, 2016

(87) PCT Pub. No.: WO2015/151053
PCT Pub. Date: Oct. 8, 2015

(65) Prior Publication Data
US 2017/0095000 A1 Apr. 6, 2017

(30) Foreign Application Priority Data
Apr. 1, 2014 (IT) .............................. BO2014A0181

(51) Int. Cl.
*A61M 15/06* (2006.01)
*H05B 1/02* (2006.01)
*A24F 47/00* (2006.01)

(52) U.S. Cl.
CPC ......... *A24F 47/008* (2013.01); *H05B 1/0244* (2013.01); *H05B 2203/021* (2013.01)

(58) Field of Classification Search
None
See application file for complete search history.

(56) References Cited

U.S. PATENT DOCUMENTS 3,911,080 A * 10/1975 Mehl ...................... B01D 53/34 204/234
4,182,743 A * 1/1980 Rainer .................. B01D 53/72 131/334
(Continued)

FOREIGN PATENT DOCUMENTS

DE 202013010359 U1 1/2014
DE 102012108477 A1 3/2014
(Continued)

OTHER PUBLICATIONS

International Search Report and Written Opinion, International Application No. PCT/IB2015/052411, dated Oct. 9, 2015.

*Primary Examiner* — Thor S Campbell
(74) *Attorney, Agent, or Firm* — Marshall, Gerstein & Borun LLP

(57) ABSTRACT

Disposable electronic-cigarette cartridge; the electronic-cigarette cartridge having: a hygroscopic plug; a liquid substance which impregnates the hygroscopic plug and is vaporized in use; and a surface covering, which is located on the outside of the hygroscopic plug, completely covers the hygroscopic plug itself, is impermeable to liquids, and is permeable to gas.

11 Claims, 3 Drawing Sheets

(56) References Cited

U.S. PATENT DOCUMENTS

| | | | | |
|---|---|---|---|---|
| 4,941,483 | A * | 7/1990 | Ridings | F24V 30/00 131/194 |
| 5,666,978 | A * | 9/1997 | Counts | A24F 47/008 131/194 |
| 8,915,254 | B2 * | 12/2014 | Monsees | A24F 47/006 131/273 |
| 2008/0092912 | A1 | 4/2008 | Robinson et al. | |
| 2012/0048266 | A1 | 3/2012 | Alelov | |
| 2012/0247494 | A1 * | 10/2012 | Oglesby | A24F 47/006 131/328 |
| 2013/0220315 | A1 | 8/2013 | Conley et al. | |
| 2013/0255702 | A1 | 10/2013 | Griffith, Jr. et al. | |
| 2014/0014126 | A1 | 1/2014 | Peleg et al. | |
| 2018/0007972 | A1 * | 1/2018 | Thorens | A61M 11/003 |

FOREIGN PATENT DOCUMENTS

| | | | |
|---|---|---|---|
| EP | 0893071 | A1 | 1/1999 |
| EP | 2022349 | A1 | 2/2009 |
| EP | 2110033 | A1 | 10/2009 |
| EP | 2468118 | A1 | 6/2012 |
| EP | 2489391 | A1 | 8/2012 |
| JP | 2012029633 | A | 2/2012 |

* cited by examiner

DISPOSABLE ELECTRONIC-CIGARETTE CARTRIDGE AND RESPECTIVE PRODUCTION METHOD

CROSS-REFERENCE TO RELATED APPLICATIONS

This is the U.S. National Phase of International Application No. PCT/IB2015/052411, filed Apr. 1, 2015, which claims the benefit of Italian Patent Application No. BO2014A000181, filed Apr. 1, 2014.

TECHNICAL FIELD

The present invention relates to a disposable electronic-cigarette cartridge and to a respective production method.

PRIOR ART

Recently disposable electronic-cigarette cartridges (i.e. disposable) have been proposed; said cartridges are filled with a viscous liquid substance containing nicotine and possible flavourings that in use is slowly volatilized (vapourized) in order to be inhaled by the smoker.

A known disposable cartridge comprises a rigid container (generally of a cylindrical shape), inside which a hygroscopic plug is housed (such as a cotton pad) that has been previously impregnated with the viscous liquid substance containing nicotine and possible flavourings; a resistor is also provided, which is thermally coupled to the hygroscopic pad (for example, the electric resistor is constituted by a wire wound around the hygroscopic pad) and in use electrical current flows through it so as to heat the hygroscopic pad and therefore cause the slow volatilization (vapourization) of the viscous liquid substance which impregnates the hygroscopic pad. Obviously, the rigid container has openings (typically on one of the two circular bases) through which the vapours generated by the volatilization (vapourization) of the liquid substance flow out from the rigid container to be inhaled by the smoker.

The production of said disposable cartridges entails producing the rigid container with an open top end, inserting the dry hygroscopic pad inside the rigid containers, filling the rigid container with a calibrated amount of the liquid substance, and then capping the rigid containers by applying to the open top end a cap permeable to vapours (i.e. a cap that prevents the liquid substance from leaking, but that does not prevent the vapour, generated by heating the liquid substance, from escaping); once the cap is applied, a corresponding adhesive label is wrapped around each cartridge to terminate the production process.

The known disposable cartridges of the type described above have some drawbacks. In the first place, mainly due to the presence of the rigid container, the known disposable cartridges are not easily biodegradable and therefore have a significant environmental impact. In addition, the known disposable cartridges are rather expensive due to the number of components of each disposable cartridge. Finally, because of their complexity, the known disposable cartridges are difficult to produce. Consequently, the production thereof is performed manually or with rudimentary machines which provide a continuous use of labour; therefore, the current production of disposable cartridges takes place in a slow manner (that is, with a low productivity) and with very variable quality (but generally modest).

DESCRIPTION OF THE INVENTION

The object of the present invention is to provide a disposable electronic-cigarette cartridge and a respective production method, the disposable cartridge of which is free from the drawbacks described above and is, at the same time, easy and inexpensive to manufacture.

According to the present invention, a disposable electronic-cigarette cartridge and a corresponding producing method, as claimed in the appended claims, are provided.

BRIEF DESCRIPTION OF THE DRAWINGS

The present invention will now be described with reference to the accompanying drawings, which illustrate a non-limitative embodiment, wherein.

PREFERRED EMBODIMENTS OF THE INVENTION

Figure 1:
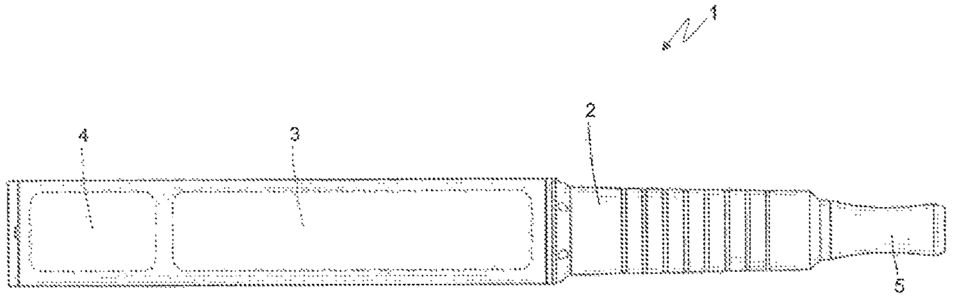
FIG. 1 is a schematic side view of an electronic-cigarette provided with a disposable cartridge made according to the present invention.

In FIG. 1 number 1 indicates as a whole a electronic-cigarette.

The electronic-cigarette comprises a tubular body 2, which has a front compartment in which a disposable cartridge 3 (i.e. for single use) is housed filled with a viscous liquid substance (for example propylene glycol) containing nicotine and possible flavourings. Furthermore, in the front compartment of the tubular body 2 a controlling device 4 is housed, which is electrically connected to the disposable cartridge 3 for controlling the heating of the disposable cartridge 3 itself so as to determine in use the slow vapourization of the liquid substance contained in the disposable cartridge 3; the vapours produced by heating the liquid substance flow along the tubular body 2 until reaching a mouthpiece 5.

Figure 2:
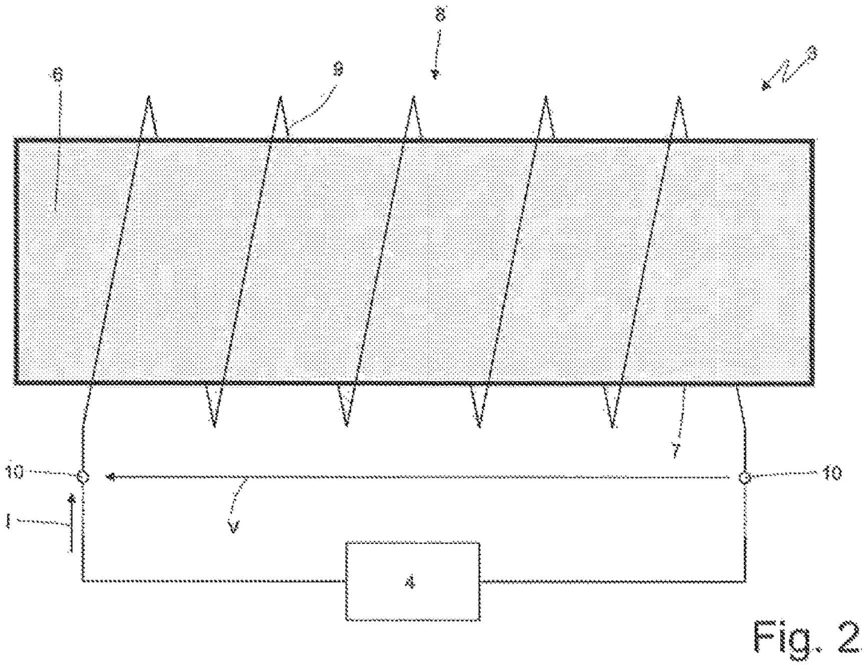
FIG. 2 is a schematic side view of a disposable cartridge of the electronic-cigarette of FIG. 1.

As shown in FIG. 2, the disposable cartridge 3 comprises a cylindrical-shaped hygroscopic pad 6 which is impregnated with the liquid substance (i.e. the hygroscopic pad 6 internally contains a certain amount of liquid substance which impregnates the hygroscopic pad 6 itself). By way of example, the pad 6 can be formed by means of hygroscopic glass and silica fibres (that resist without damage to very high temperatures above 1000° C.), or can be made from less costly materials such as cellulose acetate (commonly used to make traditional cigarette filters).

The hygroscopic pad 6 is provided with a surface covering 7, which is located on the outside of the hygroscopic pad 6 and completely covers the hygroscopic pad 6 itself. The surface covering 7 is impermeable to liquids (i.e. prevents the passage of liquids so as to prevent the liquid substance, in the liquid state, from leaking from the hygroscopic pad 6) and, at the same time, it is permeable to gas (i.e. allows the passage of gas so as to allow the outflow of the liquid substance, in the vapourous state, from the hygroscopic pad 6). It is important to note that the surface covering 7 being permeable to gas allows the passage of both vapour (outflowing from the hygroscopic pad 6), and air (inflowing to the hygroscopic pad 6 and outflowing from the hygroscopic pad 6).

By way of example, the surface covering 7 which has high impermeable capability (i.e. is impermeable to polar and apolar liquids) and transpiring (i.e. permeable to gas) is made from polytetrafluoroethylene (PTFE) thermo-mechanically expanded so as to be microporous. In essence, the coating has many microscopic holes (of the order of billions per square centimeter), each of which is much smaller (thousands of times) than a drop of water, but allows the passage of gas, making the coating at the same time impermeable and transpiring. Alternatively, the surface covering 7 is made by means of silica and inert material based nanotechnological treatments.

In the embodiment illustrated in the attached figures, the surface covering 7 adheres directly to an outer surface of the hygroscopic pad 6, i.e. the surface covering 7 is applied directly (for example as a covering paint) to the outer surface of the hygroscopic pad 6. According to an alternative and perfectly equivalent embodiment, a liner (obviously of a material at least permeable to gas) which encloses the hygroscopic pad 6 and supports the surface covering 7 is provided; in other words, the hygroscopic pad 6 is completely enclosed by the liner 7 and the surface covering is applied to the liner itself.

As shown in FIG. 2, the disposable cartridge 3 comprises an electric heating resistor 8, which is fitted (thermally) to the hygroscopic pad 6. In the embodiment illustrated in FIG. 2, the electric heating resistor 8 is constituted by a metallic conducting wire 9, which is wound in a spiral around the hygroscopic pad 6. According to a different and perfectly equivalent embodiment not illustrated, the electric heating resistor 8 is printed on the outer surface of the hygroscopic pad 6 using conductive inks (e.g. an ink of silver, carbon or copper nanoparticles). In particular, the electric heating resistor 8 rests on the surface covering 7 of the hygroscopic pad 6, i.e. in direct contact with the surface covering 7 of the hygroscopic pad 6.

The electric heating resistor 8 has two terminals (terminals, ends) 10, to which the controlling device 4 is connected; in use, the controlling device 4 applies a voltage V to the terminals 10 of the electric heating resistor 8 to circulate through the electric heating resistor 8 a current I which determines heating, by Joule effect, of the electric heating resistor 8 itself; said heating of electric heating resistor 8 itself determines the slow evapouration of the liquid substance contained in the hygroscopic pad 6 of the disposable cartridge 3.

According to a possible embodiment, the controlling device 4 estimates the actual temperature of the electric heating resistor 8, and then varies the voltage V applied to the terminals 10 of the electric heating resistor 8 according to the actual temperature of the electric heating resistor 8 (typically to maintain the actual temperature of the electric heating resistor 8 at about a predetermined desired value). In this way, the controlling device 4 avoids to excessively heat the hygroscopic pad 6 (particularly when the hygroscopic pad 6 is empty, i.e. devoid of the liquid substance due to the depletion of the liquid substance itself). According to a preferred embodiment, the controlling device 4 estimates the actual temperature of the electric heating resistor 8 as a function of an actual electric resistance of the electric heating resistor 8 (i.e. the actual electric resistance revealed at the terminals 10).

According to a possible embodiment, the controlling device 4 determines (measures or estimates) the voltage V applied to the terminals 10 of the electric heating resistor 8, determines (measures or estimates) the intensity of the current I that circulates through the electric heating resistor 8, and then calculates the actual resistance of the electric heating resistor 8 by dividing the voltage V applied to the terminals 10 of the electric heating resistor 8 by the intensity of the current I that circulates through the electric heating resistor 8. In this case, the electric heating resistor 8 estimates the actual temperature of the electric heating resistor 8 directly as a function of the actual resistance of the electric heating resistor 8.

According to a more simple and inexpensive alternative embodiment (but less accurate), the controlling device 4 compares (for example by means of a bridge), the actual electric resistance of the electric heating resistor 8 with the electric resistance of a sample electric resistor (having a value depending on the desired temperature value of the electric heating resistor 8), and then estimates the actual temperature of the electric heating resistor 8 as a function of the comparison between the actual electric resistance of the electric heating resistor 8 and the electric resistance of the specimen electric resistor. In other words, in this embodiment, the controlling device 4 varies the voltage V applied to the terminals 10 of the electric heating resistor 8 so that the actual electric resistance of the electric heating resistor 8 is identical (as much as possible) to the electric resistance of the sample electric resistor.

By controlling the temperature of the electric heating resistor 8 excessive heating of the hygroscopic pad 6 is avoided, and then the hygroscopic pad 6 itself can be made in less costly materials that cannot withstand very high temperatures. Moreover, by controlling the temperature of the electric heating resistor 8 the health of the smoker is protected, as excessive heating of the hygroscopic pad 6 it prevented (for example when the hygroscopic pad 6 is dry, i.e. devoid of liquid substance that by vapourizing limits the maximum temperature of the hygroscopic pad 6 itself), thus avoiding that the hygroscopic pad 6, subjected to high temperatures, can release gas that is potentially toxic or otherwise undesirable although harmless.

According to a possible embodiment, the controlling device 4 estimates the amount of electrical energy that has been consumed overall by the electric heating resistor 8 during heating (or the total amount of electrical energy that was absorbed by the electric heating resistor 8 from the beginning of its implementation) and then estimates the amount of liquid substance that has been evapourated as a function of the amount of electrical energy that has been consumed overall by the electric heating resistor 8 during heating. In other words, to evapourate a certain amount of liquid substance contained in the hygroscopic pad 6 of the disposable cartridge it is necessary to supply the liquid substance with a quantity of preset and substantially constant heat; so it is possible to determine a relationship between the amount of electrical energy that has been consumed overall by the electric heating resistor 8 during heating and the amount of liquid substance that has been evapourated. Thanks to this relationship, the controlling device 4 can estimate the amount of liquid substance that was evapourated and, by simply subtracting it from the amount of initial liquid substance, it can then determine the amount of liquid substance remaining in the hygroscopic pad 6 of the disposable cartridge 3. The relationship between the amount of electrical energy that has been consumed overall by the electric heating resistor 8 during heating and the amount of liquid substance that has been evapourated is generally determined experimentally.

Normally, the electrical energy absorbed by the electric heating resistor 8 during heating is estimated by integrating over time the electrical power consumed by the electric heating resistor 8 during heating; the electrical power absorbed by the electric heating resistor 8 during heating is normally calculated by multiplying the voltage V (measured or estimated) applied to the terminals 10 of the electric heating resistor 8 by the intensity (measured or estimated) of the current I that circulates through the electric heating resistor 8.

Figure 3:
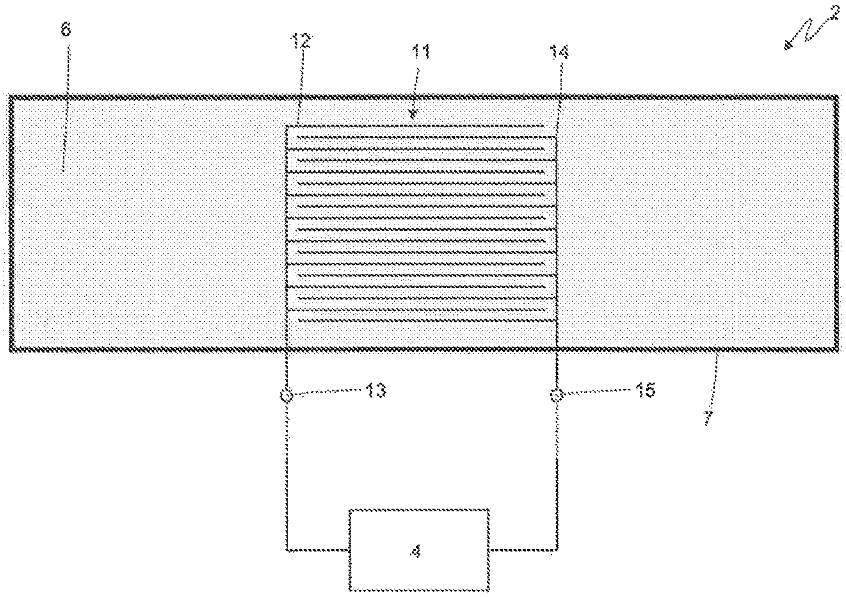
FIG. 3 is a schematic side view of the disposable cartridge of FIG. 2 with a highlighted moisture sensor.

In the embodiment illustrated in FIG. 3, the disposable cartridge 3 comprises a moisture sensor 11 fitted to the hygroscopic pad 6 of the disposable cartridge 3 for determining the content of liquid substance inside the hygroscopic pad 6 itself. The moisture sensor 11 is a capacitive type and comprises a conducting element 12, which is applied to an outer surface of the hygroscopic pad 6 and is connected to a terminal (terminal/end) 13, and a conducting element 14, which is applied to the outer surface of the hygroscopic pad 6, is electrically insulated from the conducting element 12, is located in proximity to the conducting element 12, and fishes at a terminal (terminal/end) 15. According to a preferred, but not binding, embodiment, each conducting element 12 or 14 is comb-shaped and has a plurality of teeth which penetrate without contact between the teeth of the other conducting element 14 or 12. According to a possible, but not binding, embodiment, the conducting elements 24 and 14 of the moisture sensor 11 are printed on the outer surface of the hygroscopic pad 6 using conductive inks (such as an ink of silver, carbon or copper nanoparticles).

In use, the controlling device 4 determines (measures) the actual capacitance at the end of terminals 13 and 15 and therefore according to the actual capacitance at the end of terminals 13 and 15 estimates the content of liquid substance inside the hygroscopic pad 6 of the disposable cartridge 3; in other words, the electric capacitance measured between the two terminals 13 and 15 depends upon the quantity of liquid substance inside the hygroscopic pad 6 and increases as the amount of liquid substance inside the hygroscopic pad 6 increases. The relation between the actual capacitance at the ends of the terminals 13 and 15 and the quantity of the liquid substance contained inside the hygroscopic pad 6 of the disposable cartridge 3 is normally determined in an experimental way.

The ability to estimate with high accuracy the amount of liquid substance contained inside the hygroscopic pad 6 of the disposable cartridge 3 allows to inform the user in advance when the disposable cartridge 3 is close to be completely empty avoiding the user to be caught by surprise (i.e. without a new, spare disposable cartridge 3) by the emptying of the disposable cartridge 3 in use. Also, the ability to estimate with high precision the quantity of liquid substance contained inside the hygroscopic pad 6 of the disposable cartridge 3 allows to interrupt the heating of an already emptied disposable cartridge 3 avoiding to unnecessarily heat the exhausted hygroscopic pad 6 (in this way preventing that the temperature of the hygroscopic pad 6, no longer mitigated by the latent evapouration heat of the liquid substance, can reach high values that could cause the generation of potentially toxic or otherwise unwanted although harmless volatile substances).

According to a possible, but not binding embodiment, for the production of the disposable cartridge 3 the hygroscopic pad 6 is initially prepared and then the surface covering 7 is applied to the hygroscopic pad 6 (impermeable to liquids and permeable to gas), which is located outside the hygroscopic pad 6 and completely covers the hygroscopic pad 6 itself. Once the surface covering 7 is applied to the hygroscopic pad 6, the hygroscopic pad 6 itself is impregnated with the liquid substance which vapourizes in use; in other words, the hygroscopic pad 6 is impregnated with the liquid substance after applying the surface covering 7. According to a preferred embodiment, the hygroscopic pad 6 is impregnated with the liquid substance using a needle which locally penetrates the hygroscopic pad 6 and therefore allows to inject the liquid substance directly inside the hygroscopic pad 6 overcoming the liquid barrier formed by the surface covering 7 (obviously the needle receives the liquid substance under pressure by a feed device which can for example be shaped as a syringe). Once the injection of the liquid substance inside the hygroscopic pad 6 through the needle is over, the needle is withdrawn from the hygroscopic pad 6; the small hole in the surface covering 7 determined by the penetration of the needle closes spontaneously by elastic return of the hygroscopic pad 6 and therefore does not determine appreciable loss of liquid substance from the hygroscopic pad 6.

The disposable cartridge 3 described above has numerous advantages.

In the first place, the disposable cartridge 3 described above has a very low production cost, as compared to a similar known disposable cartridge is completely devoid of an outer rigid container (i.e. completely devoid of rigid materials that require an assembly process).

The disposable cartridge 3 described above has a low environmental impact as, compared to a similar known disposable cartridge, it is entirely without external rigid container (i.e. totally devoid of rigid materials). In particular, by choosing the material that composes the hygroscopic pad 6 appropriately, the disposable cartridge 3 described above can be (almost) completely biodegradable in a relatively short time, and then in addition to being environmentally friendly may not even require any type of recycling of the used disposable cartridges 3.

The permeability of the hygroscopic pad 6 to air allows to facilitate mixing between the vapour that is released from the hygroscopic pad 6 and the outside air thus reducing the risk of scalding by steam (saturated steam transposes a large amount of latent heat, while dry air has a very low thermal conductivity and even at temperatures of hundreds of degrees does not cause damage to mucous membranes).

The invention claimed is:

1. A disposable electronic-cigarette cartridge (3);

the disposable cartridge (3) comprising:

a hygroscopic pad (6);

a liquid substance which impregnates the hygroscopic pad (6) and is vapourized in use;

a surface covering (7) which is located on the outside of the hygroscopic pad (6), completely covers the hygroscopic pad (6), is impermeable to liquid, and is permeable to gas; and a moisture sensor (11) fitted to the hygroscopic pad (6) to determine the liquid substance content of the hygroscopic pad (6).

2. A disposable cartridge (3) according to claim 1, wherein the surface covering (7) is impermeable to liquid to prevent the liquid substance from leaking in the liquid state from the hygroscopic pad (6), and is permeable to gas to allow the liquid substance to flow out in the vapour state from the hygroscopic pad (6).

3. A disposable cartridge (3) according to claim 1, wherein the surface covering (7) adheres directly to an outer surface of the hygroscopic pad (6).

4. A disposable cartridge (3) according to claim 1, and comprising a liner which encloses the hygroscopic pad (6) and supports the surface covering (7).

5. A disposable cartridge (3) according to claim 1, and comprising an electric heating resistor (8) fitted to the hygroscopic pad (6).

6. A disposable cartridge (3) according to claim 5, wherein the electric heating resistor (8) rests on the surface covering (7) of the hygroscopic pad (6).

7. A disposable cartridge (3) according to claim 1, wherein the moisture sensor (11) is a capacitive type.

8. A disposable cartridge (3) according to claim 7, wherein the moisture sensor (11) comprises:

a first conducting element (12) applied to an outer surface of the hygroscopic pad (6) and connected to a first terminal (13); and a second conducting element (14) which is applied to an outer surface of the hygroscopic pad (6), is electrically insulated from the first conducting element (12), is located close to the first conducting element (12), and is connected to a second terminal (15).

9. A disposable cartridge (3) according to claim 8, wherein each conducting element (12; 14) is comb-shaped, and has a number of teeth which penetrate, without contacting, between the teeth of the other conducting element (14; 12).

10. A disposable cartridge (3) according to claim 8, wherein the capacitance measured between the two terminals (13, 15) depends on the amount of liquid substance inside the hygroscopic pad (6), and increases alongside an increase in the amount of liquid substance inside the hygroscopic pad (6).

11. A method of producing a disposable electronic-cigarette cartridge (3); the method comprising the steps of:

preparing a hygroscopic pad (6);

impregnating the hygroscopic pad (6) with a liquid substance which is vapourized in use;

applying to the hygroscopic pad (6) a surface covering (7) which is located on the outside of the hygroscopic pad (6), completely covers the hygroscopic pad (6), is impermeable to liquid, and is permeable to gas;

wherein the hygroscopic pad (6) is impregnated with the liquid substance after the surface covering (7) is applied, and using a needle which locally penetrates the hygroscopic pad (6).

* * * * *